(12) United States Patent
Erickson et al.

(10) Patent No.: US 9,523,070 B2
(45) Date of Patent: Dec. 20, 2016

(54) PHOTOBIOREACTOR APPARATUS, METHOD AND APPLICATION

(71) Applicant: CORNELL UNIVERSITY, Ithaca, NY (US)

(72) Inventors: David Erickson, Ithaca, NY (US); Largus Angenent, Ithaca, NY (US); Devin Doud, Cortland, NY (US); Erica Jung, Ithaca, NY (US); Michael Kalontarov, Briarwood, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/770,246

(22) PCT Filed: Mar. 7, 2014

(86) PCT No.: PCT/US2014/021878
§ 371 (c)(1),
(2) Date: Aug. 25, 2015

(87) PCT Pub. No.: WO2014/164320
PCT Pub. Date: Oct. 9, 2014

(65) Prior Publication Data
US 2016/0002580 A1    Jan. 7, 2016

Related U.S. Application Data

(60) Provisional application No. 61/776,083, filed on Mar. 11, 2013.

(51) Int. Cl.
C12M 1/00        (2006.01)

(52) U.S. Cl.
CPC ............. *C12M 21/02* (2013.01); *C12M 29/00* (2013.01); *C12M 29/04* (2013.01); *C12M 29/16* (2013.01);
(Continued)

(58) Field of Classification Search
CPC ....... C12M 21/02; C12M 29/00; C12M 29/04; C12M 29/16; C12M 31/02; C12M 31/04; C12M 31/08
(Continued)

(56) References Cited

U.S. PATENT DOCUMENTS

2009/0047722 A1   2/2009  Wilkerson et al.
2009/0148931 A1   6/2009  Wilkerson et al.
(Continued)

FOREIGN PATENT DOCUMENTS

WO    2012067995 A2    5/2012

OTHER PUBLICATIONS

International Search Report and Written Opinion for International Application No. PCT/US2014/021878, International Filing Date Mar. 7, 2014, 10 pages.

*Primary Examiner* — Jonathan Hurst
(74) *Attorney, Agent, or Firm* — Bond, Schoeneck & King, PLLC; William Greener

(57) ABSTRACT

A photobioreactor includes an input light delivery component and a plurality of photobioreactor media disposed in a stacked relationship, each of which is coupled to the input light delivery component, wherein each photobioreactor medium is adapted to be inoculated with a photosynthetic, biofuel-producing culture, further wherein each photobioreactor medium includes at least one hollow fiber membrane (HFM) disposed thereon in a region that is adapted to be inoculated with the photosynthetic, biofuel-producing culture, that can transport at least one of a gas and a photobioreactor product producible by the photosynthetic, biofuel-producing culture, wherein each photobioreactor medium is characterized by an input light-scattering mechanism. A method for making a biofuel including providing a stacked photobioreactor assembly including a plurality of unit pho- (Continued)

tobioreactor mediums each of which is inoculated with a photosynthetic, biofuel-producing culture, characterized by a light scattering mechanism and including at least one hollow fiber membrane (HFM) disposed in-situ on the photobioreactor medium; providing a nutrient gas to the biofuel-producing culture via the at least one HFM; and illuminating each unit photobioreactor medium with a selected spectrum of input light via the light scattering mechanism in each unit photobioreactor medium.

22 Claims, 6 Drawing Sheets

(52) U.S. Cl.
CPC .............. *C12M 31/02* (2013.01); *C12M 31/04* (2013.01); *C12M 31/08* (2013.01)

(58) Field of Classification Search
USPC ........................................................ 435/292.1
See application file for complete search history.

(56) References Cited

U.S. PATENT DOCUMENTS

| | | | |
|---|---|---|---|
| 2010/0267104 A1* | 10/2010 | Green | C12M 21/02 435/173.1 |
| 2012/0247008 A1 | 10/2012 | Gonzalez et al. | |
| 2012/0288928 A1 | 11/2012 | Jung et al. | |
| 2013/0302869 A1* | 11/2013 | Erickson | C12M 21/02 435/292.1 |

* cited by examiner

PHOTOBIOREACTOR APPARATUS, METHOD AND APPLICATION

RELATED APPLICATION DATA

The instant application claims priority to U.S. provisional application Ser. No. 61/776,083 filed Mar. 11, 2013, the subject matter of which is incorporated herein by reference in its entirety.

BACKGROUND

Aspects and embodiments of the invention are directed to a photobioreactor and methods for producing a bioproduct using said photobioreactor; more particularly to a stacked, slab-type waveguide photobioreactor assembly and associated methods and applications thereof.

Concerns about the impact of climate change, $CO_2$ emissions, and energy security have led to widespread interest in the production of biofuels from microalgae. Microalgae have higher $CO_2$ fixation efficiencies and growth rates than other plant-based feedstocks and the potential to utilize waste-water or industrial gas wastes as nutrient sources. The most developed method for extracting biofuels from microalgae is converting their stored lipids into biodiesel, which utilizes a separation process that is very energy intensive. This has prompted the research and development of many engineered strains of cyanobacteria to directly secrete fuels such as hydrogen, ethanol, isobutyraldehyde, and other high value products.

To take advantage of these engineered strains, innovative photobioreactor (PBR) designs are required that can sustain high density cultures while enabling efficient light delivery and gas exchange. The most common reactors used in algal cultivation are open raceway ponds and tubular-type enclosed reactors. While these designs do have respective advantages, both are faced with fundamental limitations in delivery of sufficient light and $CO_2$ and extraction of products to maintain high photosynthetic rates. Uneven light distribution causes the culture to be overexposed at the surface and underexposed below the light penetration depth. To counteract this problem many approaches have been investigated including the integration of optical fibers, interaction with evanescent and plasmonic fields, and planar waveguides.

In parallel to the problem of light delivery, limitations in gas exchange and transport are also being addressed. Traditionally, gas exchange in PBRs is provided by bubbling or passive exposure to the atmosphere. Though easy to implement, these methods constrain optimal PBR geometries and operation, and limit possible culture densities. $CO_2$ delivery is limited by uneven distribution throughout the reactor volume. Maintaining a uniform distribution is important for efficient volume utilization since regions with low $CO_2$ concentration suffer from lower rates of photosynthesis. Turbulent flow mixing is a common mechanism by which $CO_2$ concentration is equilibrated. This condition requires that a large amount of energy is spent on mixing the algal cultures, up to 41% of the cultivation energy budget in some cases, and contributes to the already high energy costs of the algal cultivation process. This has motivated research into various methods for improving gas exchange coefficients and reducing the mixing energy demands in PBRs.

A recent advance in enhancing gas exchange has been the integration of hollow fiber membranes (HFMs) modules into PBRs. A HFM consists of hollow fibers with membranes that allow for gas exchange between the media inside and outside the fiber. HFMs have been used in the chemical, petrochemical, pharmaceutical and galvanic industries, and applied in such varied applications as wastewater treatment, drinking water treatment, tissue engineering, and the development of artificial organs. Recently, HFMs have shown potential to address the gas exchange challenges faced by PBRs and several lab scale reactors incorporating HFM modules have been reported. These studies have verified the potential benefits of integration of HFMs into PBRs by reporting increased biomass production, improved gas exchange, regulation of pH, and promotion of $CO_2$ fixation.

In view of the challenges and problems appreciated in the photobioreactor art and with the efficient production of biofuels using photobioreactors, the inventors have recognized the advantages and benefits to be realized by addressing these challenges and solving these problems, many of which are realized by the embodied invention directed to high density photobiorefineries with optimized light/$CO_2$ delivery and product extraction, as disclosed and claimed herein below.

DEFINITIONS AS USED HEREIN

The term 'photoautotrophic' means an organism capable of synthesizing its own food from inorganic substances using light as an energy source, including but not limited to bacteria and algae, and which is capable of producing a bioproduct biomass, biofuel, etc.) in an embodied photobioreactor.

The term 'about' means the amount of the specified quantity plus/minus a fractional amount (e.g., ±10%, ±9%, ±8%, ±7%, ±6%, ±5%, ±4%, ±3%, ±2%, ±1%, etc.) thereof that a person skilled in the art would recognize as typical and reasonable for that particular quantity or measurement.

The term 'substantially' means as close to or similar to the specified term being modified as a person skilled in the art would recognize as typical and reasonable; for e.g., within typical manufacturing and/or assembly tolerances, as opposed to being intentionally different by design and implementation or. For example, 'light substantially only in the visible spectrum' as may be used herein means 'light only in the visible spectrum' to the degree available by appropriate optical filters or other mechanisms intended to allow only visible light and to exclude light in non-visible spectra.

SUMMARY

An aspect of the invention is a photobioreactor that includes an input light delivery component and a plurality of slab waveguide photobioreactor units disposed in a stacked relationship coupled to the input light delivery component, wherein each slab waveguide photobioreactor unit is adapted to be inoculated with a photoautotrophic culture, further wherein each slab waveguide photobioreactor unit includes at least one hollow fiber membrane (HFM) disposed thereon in a region that is adapted to be inoculated with the photoautotrophic culture, that can transport at least one of a fluid (gas) and a photobioreactor product producible by the photoautotrophic culture, wherein each slab waveguide photobioreactor unit is characterized by an input light-scattering mechanism. According to various exemplary, non-limiting embodiments, the photobioreactor may include the following additional features, limitations, and/or characteristics, alone or in combination:

wherein the input light-scattering mechanism comprises a gradient distribution of light scattering locations across the slab waveguide surface;

wherein the at least one HFM is disposed substantially parallel to a light input edge of each slab waveguide photobioreactor unit;

wherein the at least one HFM consists of a plurality of HFMs disposed in a spaced, parallel relationship;

wherein the light-scattering mechanism is at least one of a plurality of surface structures and trenches on/in each slab waveguide photobioreactor unit;

wherein the plurality of surface structures and/or trenches comprise a gradient distribution of light scattering locations across the slab waveguide surface;

wherein the input light delivery component comprises an input light spectral filter;

wherein the input light delivery component further comprises a solar collector coupled to the input light filter via an optical fiber;

wherein the spectral filter is configured to provide at least one output spectral bandwidth and at least one other different output spectral bandwidth;

wherein the at least one output spectral bandwidth is in the visible spectrum and the at least one other different output spectral bandwidth is in either the UV spectrum or the UV and IR spectra;

further comprising a solar-powered system optically coupled to the at least one other different output spectral bandwidth;

wherein the spectral filter is a dichroic mirror;

wherein the spectral filter is configured to transmit substantially only light in the visible spectrum or substantially only light in either the UV spectrum or the UV and IR spectra;

further comprising a pumping system coupled to the at least one HFM to provide an active fluid flow through the HFM.

An aspect of the invention is a method for making a bioproduct from a photoautotroph, including the steps of providing a photobioreactor including a plurality of slab waveguide-type photobioreactor units each of which is inoculated with a non-circulating, photoautotrophic culture, each slab waveguide-type photobioreactor unit being characterized by a light scattering mechanism and including at least one hollow fiber membrane (HFM) disposed in-situ on the photobioreactor medium, each slab waveguide-type photobioreactor unit being coupled to a spectral input light filter; providing a fluid to the photoautotrophic culture via the at least one HFM; and illuminating each slab waveguide-type photobioreactor unit with a selected spectrum of input light via the light scattering mechanism in each slab waveguide-type photobioreactor unit. According to various exemplary, non-limiting embodiments, the method may include the following additional steps, features, limitations, and/or characteristics, alone or in combination:

removing a bioproduct produced by the photoautotrophic culture via the at least one HFM;

further comprising providing the fluid to the photoautotrophic culture via a plurality of HFMs disposed in a spaced, parallel relationship;

wherein the selected spectrum of input light is sunlight;

comprising illuminating each slab waveguide-type photobioreactor unit with light substantially only in either the UV spectrum or the UV and IR spectra;

comprising providing the fluid under a positive pressure;

further comprising illuminating each slab waveguide-type photobioreactor unit with light in either a) substantially only the UV spectrum or the UV and IR spectra and b) the visible spectrum and illuminating a separate solar-powered system with the light not used to illuminate each slab waveguide-type photobioreactor unit;

wherein the fluid is $CO_2$.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

DETAILED DESCRIPTION OF NON-LIMITING, EXEMPLARY EMBODIMENTS

Figure 1:
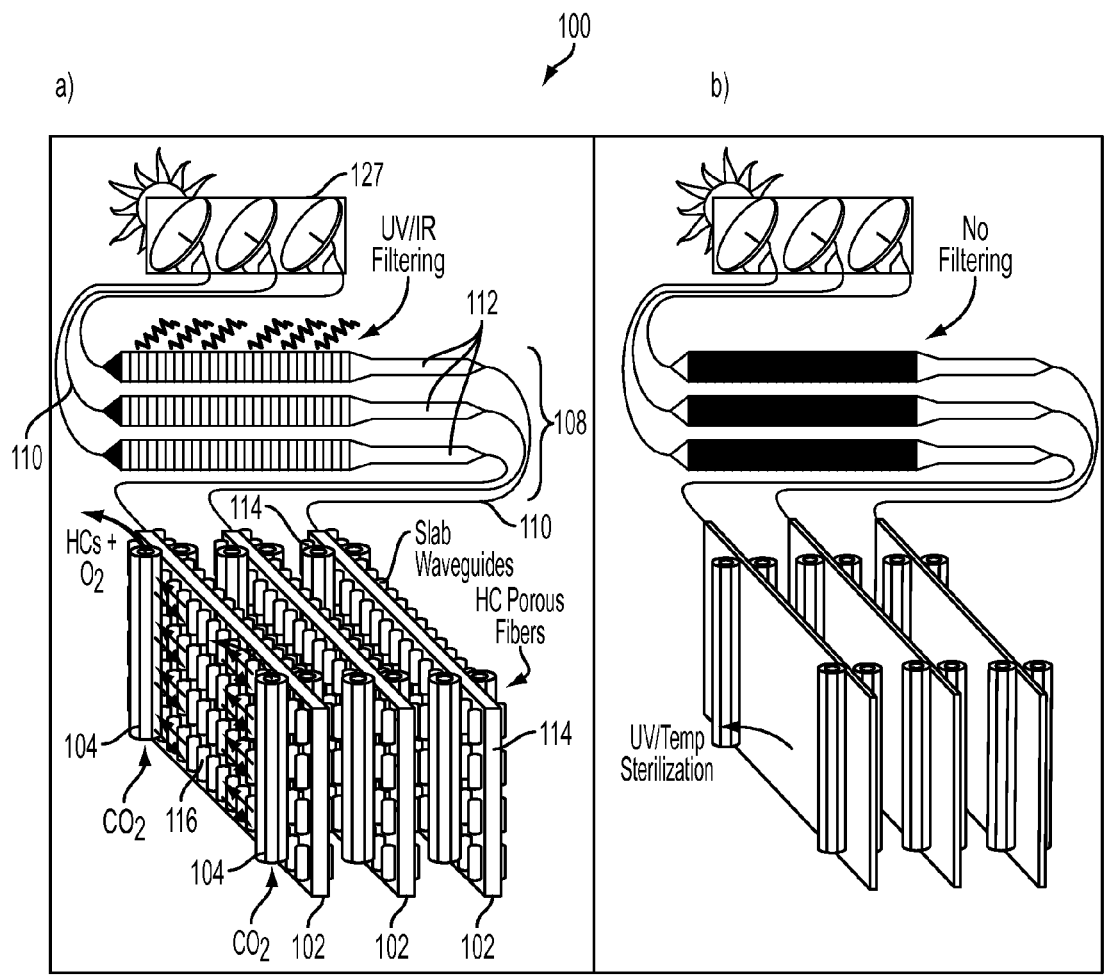
FIG. 1: a) schematically shows the components of a photobioreactor assembly in a bioproduct-producing mode; b) schematically shows the components of a photobioreactor assembly in an in-situ sterilization mode, according to non-limiting, illustrative embodiments of the invention.

An embodiment of the invention is a high density photobiorefinery providing enhanced, if not optimized, light/$CO_2$ delivery and bioproduct extraction. FIG. 1a schematically illustrates the components of an exemplary photobioreactor 100. The illustrated photobioreactor 100 includes a plurality (three as shown) of solid-state, slab waveguide photobioreactor (PBR) units 102, each PBR one or more hollow fiber membranes (HFMs) 104 disposed thereon, and a light delivery component 108 further including optical fiber waveguides 110 and spectral filters 112. As further illustrated, the optical fiber waveguides are optically coupled to the transverse edge regions 114 of respective PBRs. Structural characteristics of the PBRs, discussed in greater detail herein below, facilitate light entering the edge regions to scatter within the slab waveguide and uniformly irradiate a photoautotrophic culture 116 that has been disposed on one or both planar faces of the PBRs.

In prototype designs, each solid-state slab waveguide PBR 102 consisted of a flat, thin sheet (square/rectangular) of optically transmitting plastic with parallel faces and flat, transverse and lateral perimetal edge regions. It will be appreciated that a variety of other light transmitting materials (e.g., glass, others) would be suitable for the slab waveguide PBR units depending on size, shape, weight, capacity, and other design considerations. One or more HFM was disposed on the one or both faces of each PBR and oriented parallel to the transverse (input light-receiving) edge regions as illustrated. HFM size and spacing can be optimized as appropriate. The PBRs including the HFMs were arranged in a parallel, stacked relationship in an appropriate housing as shown. Each unit PBR assembly (slab waveguide photobioreactor unit and HFM(s)) and/or the entire stacked assembly was appropriately covered and sealed to form a closed, or closed, bioreactors (not shown for clarity). The faces of the PBRs were inoculated with an appropriate photoautotrophic culture.

In the illustrated aspect, solar collectors 127 were used to collect broad spectrum sunlight, which was channeled into and out of spectral filters 112 via optical fibers 110. The spectral filters could controllably pass light either in the visible spectrum to enable photosynthesis of the photoautotrophic culture on the PBR face(s) while substantially blocking IR and/or UV spectra or, substantially block light in the visible spectrum and pass substantially only IR and/or UV spectra to the PBR units for sterilization of the PBR as further described below. Light spectra not transmitted to the PBR may be diverted to a different solar-powered system such as, but not limited to, a solar-PV or solar heating system.

Continuous operation of photobioreactors often ends in heterotrophic contamination of photoautotrophic cultures. Addressing this contamination usually requires dismantling of reactor components, chemical disinfection, and rinsing with large volumes of water before operation can resume. The network of light delivering waveguides 110 to the PBR units and the internal scattering of the delivered IR and/or UV spectra afford a large advantage for photobioreactor sterilization compared to current procedures for disinfecting PBRs. Because the photobioreactor is already equipped with the scattering infrastructure to deliver light, this passive, in-situ sterilization of the entire photobioreactor volume by UV light, or a combination of UV/IR, is possible. Sterilization of the condensed PBR can be easily achieved without dismantling the reactor by simply blocking the photosynthetic-enabling (visible) spectrum and passing substantially only the UV or UV/IR spectra, or by connecting the light collection fibers to an artificial UV source. Following this, UV or UV/IR is delivered to the entire volume of the contained reactor for sterilization. Because this process allows the reactor to remain intact, it also reduces risk of future contamination. Sterilization by this method is essentially free as labor is minimized, wastes are eliminated, and sunlight need be the only required component. A sterilized photobioreactor is schematically illustrated in FIG. 1b.

Light delivery techniques that can overcome the limits of optical dark zones without requiring active mixing and sustain high density algal cultures would improve both cost and performance of algae-based photobioreactors. In highly dense algal cultures, the algae shadow themselves, preventing the light from penetrating through the depth. Algae growth is highly dependent on light intensity; overexposure to sunlight creates reactive oxygen species that can damage the photosynthetic machinery, whereas underexposure is insufficient for growth. Many innovative designs that incorporate larger surface areas, surface-plasmon-based light backscattering, and evanescent excitation (FIG. 6a) to better distribute light in the photobioreactor have been previously reported.

Figure 6:
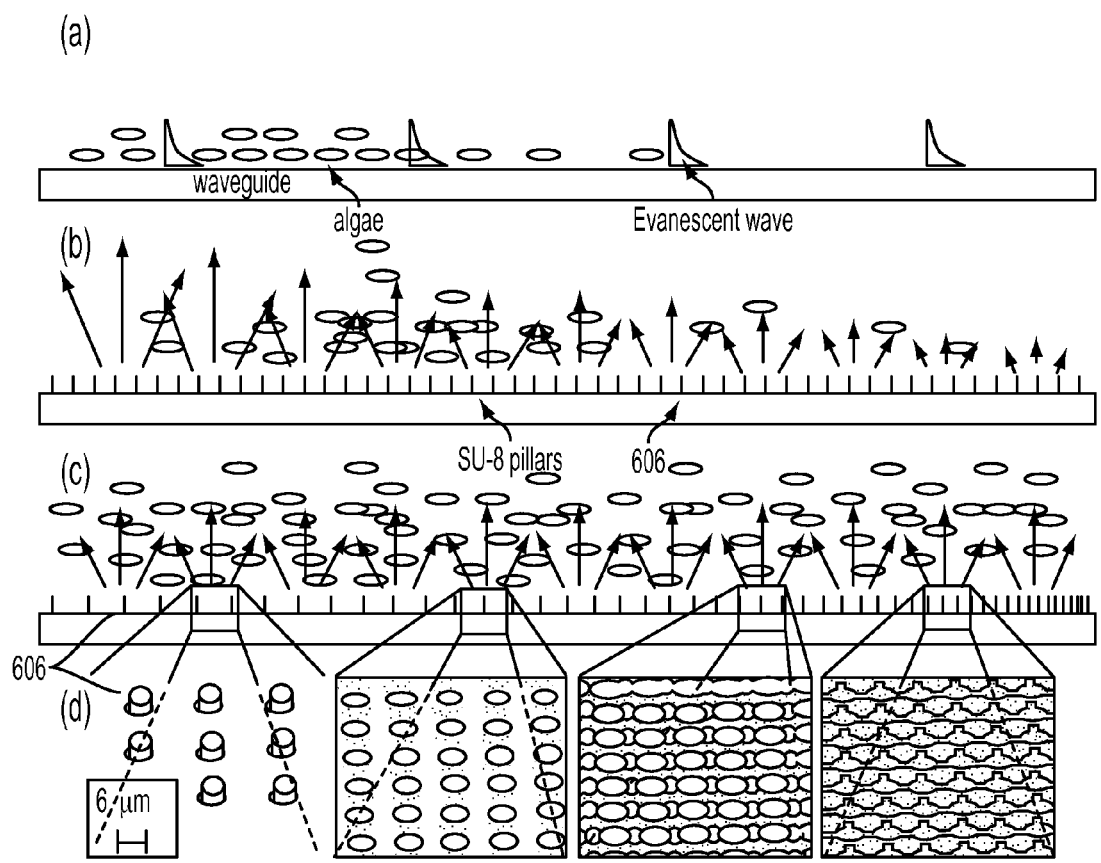
FIG. 6 illustrates the effects of light distribution and light scatterer distribution on slab waveguides for algal cultivation; (a) Algae growth excited via evanescent waves showing growth confined close to the surface of the waveguide; (b) Uniform distribution of scatterers (surface pillars) results in non-uniform illumination (and growth) across the length of the reactor; (c) Spatially varying the distribution of pillars results in more uniform illumination (and growth) along the length of the reactor; (d) SEMs of pillar scatterers at varying densities, from left to right as per FIG. 6c, down the length of the reactor.

As disclosed herein, controlled light-scattering from internal waveguides is employed to eliminate the optical dark zones in the photoautotrophic culture on the slab waveguide surface, and also for more efficacious sterilization. In this type of scheme, light is transported into the depth of the culture using waveguides where it is released into the algal culture through various scattering mechanisms. Similar methodologies have long been employed for a number of industrial applications, most notably in edge-lit LED displays. As a result, there are numerous scattering schemes that have already been developed and characterized including: the use of index-mismatched materials on the surface of the waveguide, embedded nanoparticles or other defects inside the waveguide, and shape distortions in the waveguides themselves. The inventors have previously demonstrated algae growth using evanescent excitation in optofluidic reactors using large vertically assembled slab-waveguides to scatter light into media. However, algal growth was not uniform across the length of the reactors likely due to the decay of the intensity of the internally transmitting light in the waveguide as shown in FIG. 6(a).

Figure 2:
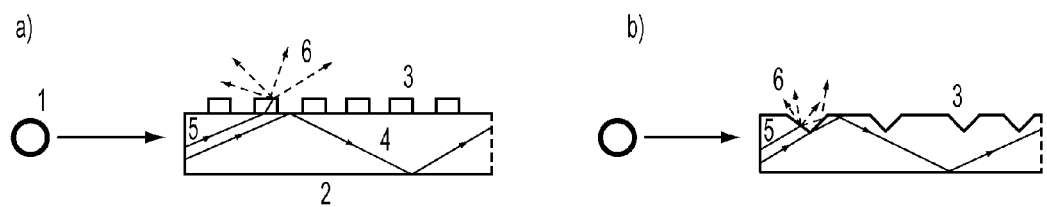
FIG. 2 schematically shows alternative light scattering mechanisms of a slab-wave guide photobioreactor unit; a) SU-8 pillar scatterers on slab-wave guide surface; b) trenches in the slab-wave guide surface, according to non-limiting, illustrative aspects of the invention.

It is intended that light input to a leading transverse edge region of a PBR unit propagate within the PBR unit via total internal reflection (TIR). To irradiate the culture-inoculated face(s) of each PBR unit, optical scatterers are incorporated onto and/or into the faces thereof. This is schematically illustrated in FIGS. 2(a, b), which respectively show pillar-type scattering structures 3-1 on the face surface of the PBR unit and trench-type scattering structures 3-2 in the face surface of the PBR unit, respectively. Briefly, when a ray of light 5 propagating inside the PBR unit traces onto an optical scatterer 3, it is able to exit from the slab-waveguide (6) in that region and be available, e.g., to the photoautotrophic culture because the optical scatterers act like index mismatches for the light to escape the face of the waveguide.

In a prototype design, the inventors used a collimated LED 1 for the light source, which was coupled into a micro-coverslip 2 of size 0 (thickness 0.085-0.130 mm) and dimension 24 mm×60 mm, which functioned as the actual slab-waveguide PBR unit. The pillars 3 were fabricated of SU-8 from standard photo-lithography techniques using SU8-2000 series. The SU-8 pillars were 2 μm thick and had square geometries of 2 μm by 2 μm. The density of the SU-8 pillar scatterers on the surface varied from 2% coverage to 50% coverage to allow for uniform lighting. The trenches 3 in FIG. 2(*b*) were added to the slab waveguide through scratching via sandpaper. Other known techniques for providing trenches or other effective scattering structures created by, e.g., chemical etching, may also be used. As will be described further below, optimum experimental results were obtained when the scattering mechanism along the light propagation direction of the slab waveguide exhibited a gradient variation as illustrated and shown in FIGS. 6*c*, 6*d* for exemplary SU-8 pillar structures 606.

More generally, when light strikes a plane interface from a material of lower to higher refractive index, part of the light is transmitted and reflected according to the Fresnel equations. For a thin layer of a higher index material on top of a glass slab-waveguide where the angle of incidence is equal to the angle of reflection ($\theta_i = \theta_r$) and the polarization does not change, the transmission and reflectance coefficients will not change for the case of a perfectly single-mode, monochromatic input. For periodically placed structures 606 of the higher index material like SU-8 as illustrated in FIG. 6*b*, however, the light coupling into the pillars and back into the waveguide may be significant. Nonetheless, as long as the coupling coefficient is low, both the intensity of the internally reflected wave and the transmitting scattered wave will decrease exponentially along the length of the waveguide as illustrated.

Experiments performed by the inventors showed that even with a single pillar under a single-mode, monochromatic wave of incidence, the resulting transmitted wave had an angular profile, which would be affected by the angle of incidence of the internally reflecting wave in the slab waveguide. The angular scattering profile was empirically measured under different input angles and at two different places on the slab-waveguide. As the input angle increased, the angular scattering profile became more perpendicular to the waveguide.

For the design of an edge-lit LCD display, only the narrower range of scattering angles perpendicular to the waveguide, which would be visible to an observer in the far-field, need to be considered. However, in a photobioreactor the algal culture will be in direct contact with the pillars and may have very small penetration depth. Therefore, the design of a slab waveguide bioreactor must take into account the entire range of scattering angles. This is especially true if the input source is incoherent, multimode, and multi-angled such as for an LED source.

Figure 7:
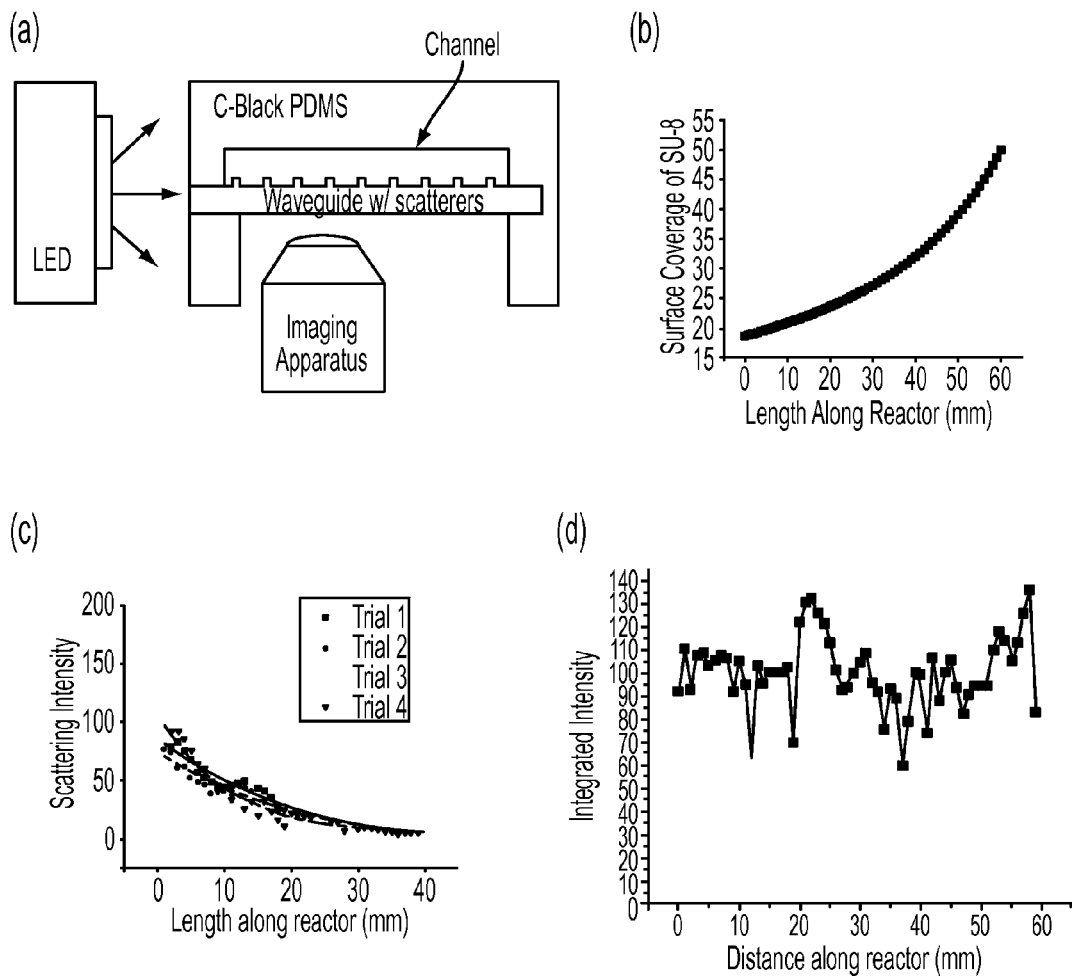
FIG. 7 shows experimental results characterizing longitudinal scattering illumination in shallow dye channels; (a) Schematic of shallow channel dye experiment; (b) graph showing the gradient variation of the surface coverage of scattering points (pillars) along the length of the reactor providing substantially uniform scattering; (c) the scattering along the length of the shallow dye channel when the sample had uniform surface coverage of scatterers of 25%; (d) the scattering along the length of the shallow dye channel when the sample had gradient surface coverage of pillars as in FIG. 7b.

In order to insure uniformity of illumination (equivalent to integrating over the angular scattering profile), shallow channel dye experiments were conducted in reactors with depths of 300 μm to simulate a thick biofilm, as shown in FIG. 7(*a*). These experiments were conducted under conditions that were to be mirrored in the final bacteria experiments. The light scattering structures were made from SU-8, a negative photoresist commonly used in photolithography. It is reasonable to assume that each internally transmitting angle, $\theta$, has a different extinction coefficient, $k(\theta)$ that remains constant when there is a uniform density of scatterers along the length of the reactor. It was found that even the scattering intensity of the broad-angled, multimode LED source used, when integrated over the range of its various angular profiles for different transmission angles, could be well modeled with an integrated extinction coefficient, $k_{int}$ such that, $$S(x) = \int d\theta A(\theta) e^{-k(\theta)x} \cong A e^{-k_{int}x} \quad (1)$$

where $S(x)$ is the scattering intensity integrated over the various angles along the length of the slab waveguide and A is a constant. This is illustrated in FIG. 7(*c*).

The extinction coefficients were found to vary linearly with the density of scatterers present on the surface for low density surface scatterers:

$$k(sc) = \frac{k_i}{sc_i} * sc \quad (2)$$

where sc is the surface coverage of the scatterers, $k_i$ is the extinction coefficient for a sample with associated surface coverage $sc_i$. It was assumed that this would hold true for higher densities of surface scatterers as well. For a pillar coverage of 25%, the associated $k_{int}$ was found to be equal to −0.028/mm.

For a scattering scheme where the extinction coefficients can be carefully controlled, it should vary as:

$$K(x) = 1 \bigg/ \left(\frac{1}{k_0} - x\right) \quad (3)$$

to achieve uniform scattering intensity across the length of the waveguide, and $$k_0 = k_{max}/(1 + L * k_{max}) \quad (4)$$

where L is the length of the waveguide and $k_{max}$ is the extinction coefficient at the end of the waveguide, which is also the maximum extinction coefficient. Using equations (2) and (3), one can derive the surface coverage of pillars required to achieve uniform scattering as:

$$SC(x) = 1 \bigg/ \left(\frac{1}{k_0} - x\right) * \frac{k_i}{sc_i}. \quad (5)$$

The highest surface coverage of pillars that was achieved was at 50% coverage. Beyond this coverage, the pillars formed a film on the glass that would peel off the surface due to poor adhesion. Using this as the highest surface coverage, we were able to show relatively uniform scattering intensity across the length of the shallow channel dye reactors of 6 cm, as shown in FIG. 7(*d*) using samples with gradient coverage described in equation (5) and graphed in FIG. 7(*b*).

It will be appreciated that there are industrial alternatives to SU-8 that are easier to employ and less expensive to produce, such as e.g., hot embossing. These industrial alternatives could make producing such waveguides for algal cultivation mass producible allowing for the potential of competitive photobioreactor technology.

Figure 4:
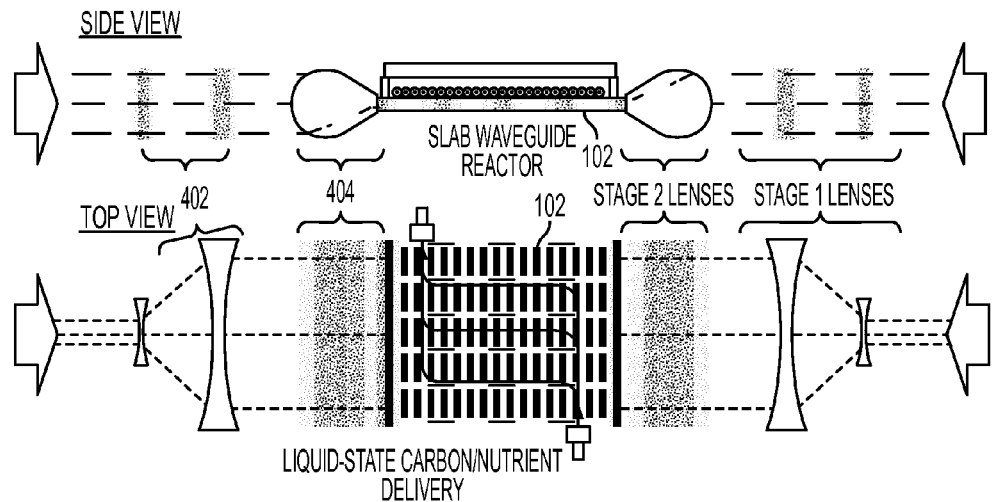
FIG. 4 schematically shows a technique for light delivery to a slab-wave guide photobioreactor, according to a non-limiting, illustrative aspect of the invention.

FIG. 4 shows an alternative structure and technique for improving the light delivery characteristics to the slab waveguide photobioreactors. Here, a first lens stage 402 comprising a cylindrical lens can be used to distribute the light intensity evenly along the transverse edge 114 of the slab waveguide 102. A second lens stage 404 comprising a cylindrical lens can then be used to focus the light incident on the reactor directly into the waveguides. Light can also be coupled into both ends of the waveguide to enhance uniformity along the depth access of the waveguide. This may be advantageous because higher density cultures will absorb a greater percentage of the incoming light resulting in a decreasing intensity with distance from the excitation point.

Figure 3:
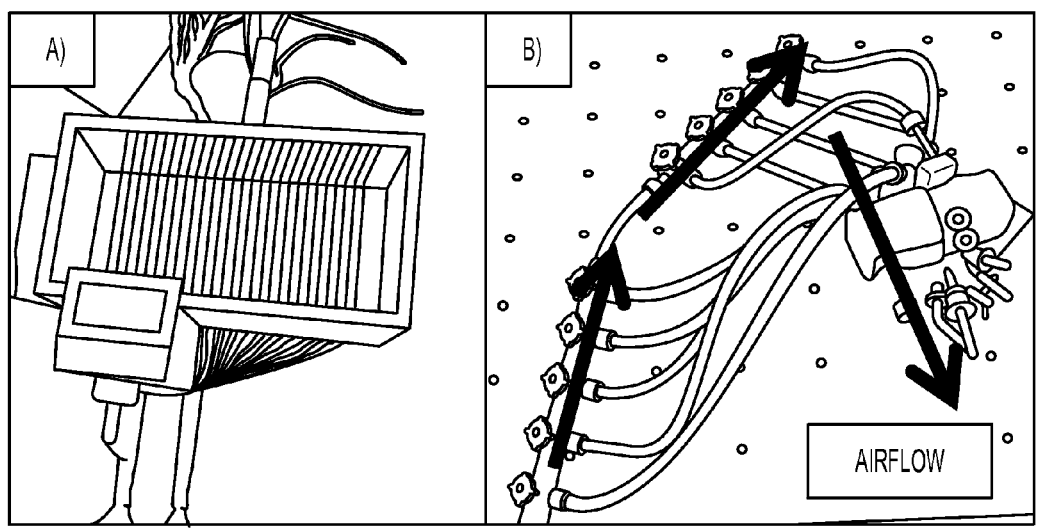
FIG. 3: (A) Construction of 10-stack photobioreactor with HFMs; (B) Pressurized ('active') reactor with airflow path indicated, according to non-limiting, illustrative aspects of the invention.
Figure 5:
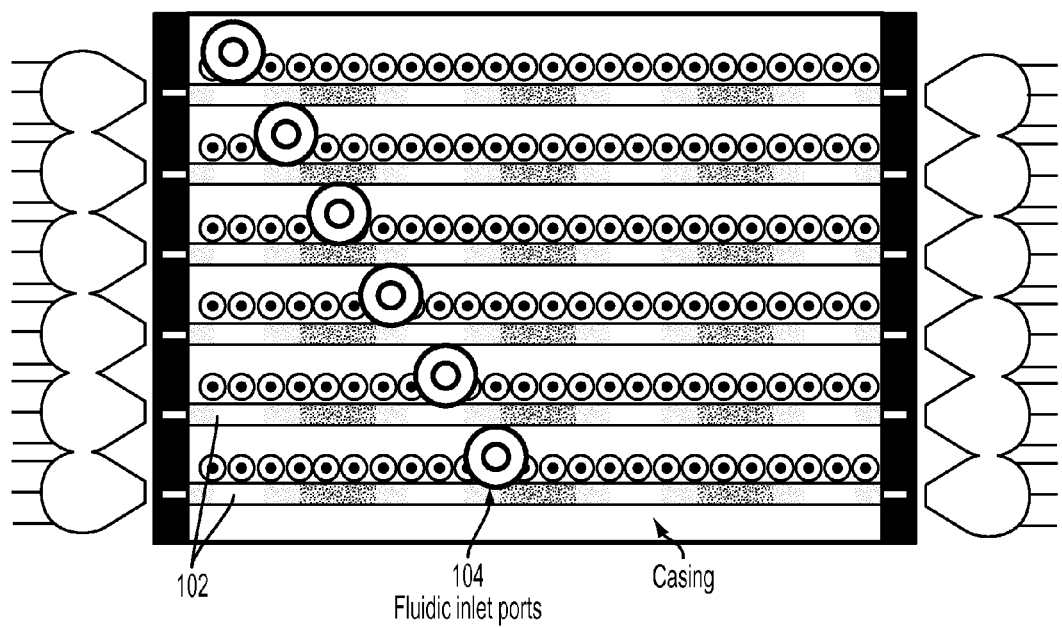
FIG. 5 schematically shows a side cross sectional view of a portion of a stacked, slab-wave guide photobioreactor, according to a non-limiting, illustrative aspect of the invention.

FIG. 5 schematically shows a side cross sectional view of a plurality of stacked, photoautotrophic culture-inoculated slab waveguide PBR units 102 each including an HFM 104. Pressurized lines can be coupled to the inlet ends of the HFMs to actively deliver $CO_2$ to the culture, remove $O_2$, and capture compatible gaseous photobioreactor products. FIG. 3(A) shows the construction of a 10 stack 'active' (pressurized) photobioreactor with hollow fibers. FIG. 3(B) shows pressurized lines and the direction of active flow through the photobioreactor.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

We claim:

1. A photobioreactor, comprising:
an input light delivery component including a spectral filter; and
a plurality of slab waveguide photobioreactor units disposed in a stacked relationship, each of which is coupled to the input light delivery component,
wherein each slab waveguide photobioreactor unit is adapted to be inoculated with a photoautotrophic culture, further wherein each slab waveguide photobioreactor unit includes at least one hollow fiber membrane (HFM) disposed thereon in a region that is adapted to be inoculated with the photoautotrophic culture, that can transport at least one of a fluid and a photobioreactor product producible by the photoautotrophic culture, further wherein each slab waveguide photobioreactor unit is characterized by an input light-scattering mechanism.

2. The photobioreactor of claim 1, wherein the input light-scattering mechanism comprises a gradient distribution of light scattering locations across the slab waveguide surface.

3. The photobioreactor of claim 1, wherein the at least one HFM is disposed transversely to a light input edge of the slab waveguide photobioreactor units.

4. The photobioreactor of claim 3, wherein the at least one HFM consists of a plurality of HFMs disposed in a spaced, parallel relationship.

5. The photobioreactor of claim 1, wherein each of the slab waveguide photobioreactor units is adapted to propagate input light via total internal reflection and the light-scattering mechanism is at least one of a plurality of surface structures and trenches on/in each of the slab waveguide photobioreactor units.

6. The photobioreactor of claim 5, wherein the plurality of surface structures and/or trenches have a gradient distribution over the slab waveguide surface.

7. The photobioreactor of claim 1, wherein the input light delivery component comprises an optical fiber coupled to the spectral filter.

8. The photobioreactor of claim 7, wherein the input light delivery component further comprises a solar collector coupled to the optical fiber and the spectral filter.

9. The photobioreactor of claim 1, wherein the spectral filter is configured to provide at least one output spectral bandwidth and at least one other different output spectral bandwidth.

10. The photobioreactor of claim 9, wherein the at least one output spectral bandwidth is in the visible spectrum and the at least one other different output spectral bandwidth is in either the UV spectrum or the UV and IR spectra.

11. The photobioreactor of claim 9, further comprising a solar-powered system optically coupled to the at least one other different output spectral bandwidth.

12. The photobioreactor of claim 9, wherein the spectral filter is a dichroic mirror.

13. The photobioreactor of claim 1, wherein the spectral filter is configured to transmit light substantially in the visible spectrum or light in substantially either the UV spectrum or the UV and IR spectra.

14. The photobioreactor of claim 1, further comprising a fluid pumping system coupled to the at least one HFM to provide an active fluid flow through the HFM.

15. A method for making a bioproduct from a photoautotroph, comprising:
providing a photobioreactor including a plurality of slab waveguide photobioreactor units each of which is inoculated with a non-circulating, photoautotrophic culture, each slab waveguide photobioreactor unit being characterized by a light scattering mechanism and including at least one hollow fiber membrane (HFM) disposed in-situ on the photobioreactor medium, each slab waveguide photobioreactor unit being coupled to a spectral input light filter;
providing a fluid to the photoautotrophic culture via the at least one HFM; and
illuminating each slab waveguide photobioreactor unit with a selected spectrum of input light via the light scattering mechanism in each slab waveguide-type photobioreactor unit.

16. The method of claim 15, further comprising removing a bioproduct produced by the photoautotrophic culture via the at least one HFM.

17. The method of claim 15, further comprising providing the fluid to the photoautotrophic culture via a plurality of HFMs disposed in a spaced, parallel relationship.

18. The method of claim 15, wherein the selected spectrum of input light is sunlight.

19. The method of claim 15, comprising illuminating each slab waveguide photobioreactor unit with light in substantially either the UV spectrum or the UV and IR spectra.

20. The method of claim 15, further comprising illuminating each slab waveguide photobioreactor unit with light in either a) substantially the UV spectrum or the UV and IR spectra and b) the visible spectrum and illuminating a separate solar-powered system with the light not used to illuminate each slab waveguide photobioreactor unit.

21. The method of claim 15, comprising providing the fluid under a positive pressure.

22. The method of claim 15, wherein the fluid is CO2.

\* \* \* \* \*

UNITED STATES PATENT AND TRADEMARK OFFICE
CERTIFICATE OF CORRECTION

Page 1 of 1

| | |
|---|---|
| PATENT NO. | : 9,523,070 B2 |
| APPLICATION NO. | : 14/770246 |
| DATED | : December 20, 2016 |
| INVENTOR(S) | : Erickson et al. |

It is certified that error appears in the above-identified patent and that said Letters Patent is hereby corrected as shown below:

In the Specification

Column 1, after the "RELATED APPLICATION DATA Paragraph", between Lines 9 and 10, please insert the following:

--STATEMENT REGARDING FEDERALLY SPONSORED RESEARCH OR DEVELOPMENT

This invention was made with government support under DE-AR0000312 awarded by the Department of Energy and 0846489 awarded by National Science Foundation. The government has certain rights in the invention.--

Signed and Sealed this
Seventh Day of March, 2017

Michelle K. Lee
*Director of the United States Patent and Trademark Office*